US006801877B2

(12) United States Patent
Schiltz et al.

(10) Patent No.: US 6,801,877 B2
(45) Date of Patent: Oct. 5, 2004

(54) PORTABLE, SELF-CONTAINED DATA COLLECTION SYSTEMS AND METHODS

(75) Inventors: Richard L. Schiltz, Hamilton, OH (US); Andrew J. Bates, Somerset (GB); Jeffery P. Watkins, Cincinnati, OH (US)

(73) Assignee: Entek IRD International Corporation, Milford, OH (US)

( * ) Notice: Subject to any disclaimer, the term of this patent is extended or adjusted under 35 U.S.C. 154(b) by 0 days.

(21) Appl. No.: 10/178,034

(22) Filed: Jun. 21, 2002

(65) Prior Publication Data

US 2002/0188411 A1 Dec. 12, 2002

Related U.S. Application Data

(62) Division of application No. 09/152,429, filed on Sep. 14, 1998, now Pat. No. 6,411,921, which is a continuation of application No. 08/526,981, filed on Sep. 12, 1995, now Pat. No. 5,808,903.

(51) Int. Cl.[7] .............................................. G06F 17/00
(52) U.S. Cl. ......................... 702/184; 702/183; 702/56
(58) Field of Search ................... 702/56, 184, 33–36, 702/39, 63, 73–75, 80, 103–105, 113–116, 121–123, 141, 182–186, 189, FOR 107, FOR 108, FOR 170, FOR 123–FOR 125, FOR 135, FOR 136, FOR 151, FOR 171; 708/139, 105, 104, 109; 340/683, 679, 680, 682, 669; 73/570, 602, 659, 660, 579, 788–796; 710/62–64, 69, 72–74; 235/472.01, 442, 493, 325, 376, 380, 472.03, 440, 441; 346/33 MC, 150.1, 3, 33 R

(56) References Cited

U.S. PATENT DOCUMENTS 3,732,631 A   5/1973   Petrovick ..................... 434/265

3,762,397 A   10/1973   Cage ........................... 128/700
4,520,674 A * 6/1985   Canada et al. ................. 73/660

(List continued on next page.)

FOREIGN PATENT DOCUMENTS

JP            7253352            10/1995

OTHER PUBLICATIONS

EMONITOR for Windows User's Guide, 1994, Entek Scientific Corporation, Second Edition, pp. 9–1, 9–3, 9–4, 9–31, 9–34, 9–35, 9–36. (No month).*
Computational Systems Incorporated, *Predictive Maintenance Instrumentation; Continuous Machinery Monitoring Systems, Dynamic Signal Analyzers, Diagnostic Field Services and Training, Customer Support*, Company and Product Brochure, 1991 (No Month) 26 pages.

(List continued on next page.)

*Primary Examiner*—Hal D Wachsman
(74) *Attorney, Agent, or Firm*—Wood, Herron & Evans, LLP

(57) ABSTRACT

A portable self-contained data collection system for measuring and collecting vibration data from machines includes an accelerometer coupled to the analog input of a data acquisition card that samples and digitizes the analog signal to produce a time domain digital signal. The data acquisition card output is coupled to a battery-powered portable computer that includes a database having machine identifications and associated measurement parameters. The portable computer processes the time domain digital signal according to the measurement parameters associated with a selected machine identification, and produces a frequency domain digital signal by performing a Fast Fourier Transform and other digital signal processing operations. The frequency domain signal is also analyzed in the portable computer to produce predictive maintenance information. A power supply for supplying power to the accelerometer is also included.

78 Claims, 9 Drawing Sheets

U.S. PATENT DOCUMENTS

| | | | |
|---|---|---|---|
| 4,612,620 A | 9/1986 | Davis et al. ............ | 364/551.01 |
| 4,885,707 A | 12/1989 | Nichol et al. ................. | 73/660 |
| 5,056,145 A | 10/1991 | Yamamoto et al. ........... | 381/51 |
| 5,122,970 A | 6/1992 | Gilbert et al. .............. | 364/508 |
| 5,210,704 A | 5/1993 | Husseiny ............... | 364/551.01 |
| 5,224,060 A | 6/1993 | Ma ............................. | 708/107 |
| 5,251,151 A * | 10/1993 | Demjanenko et al. ........ | 702/56 |
| 5,285,437 A | 2/1994 | Yokota et al. ................ | 369/64 |
| 5,357,091 A * | 10/1994 | Ozawa et al. ............... | 235/380 |
| 5,399,844 A | 3/1995 | Holland ...................... | 234/375 |
| 5,497,464 A | 3/1996 | Yeh ......................... | 364/708.1 |
| 5,541,860 A | 7/1996 | Takei et al. ................. | 364/566 |
| 5,602,749 A * | 2/1997 | Vosburgh .................... | 700/174 |
| 5,633,811 A * | 5/1997 | Canada et al. ................ | 702/56 |
| 5,808,903 A | 9/1998 | Schiltz et al. .............. | 364/508 |
| 5,822,230 A * | 10/1998 | Kikinis et al. ............. | 708/109 |
| 5,956,658 A * | 9/1999 | McMahon ................... | 702/83 |
| 6,041,374 A * | 3/2000 | Postman et al. .............. | 710/73 |
| 6,411,921 B1 | 6/2002 | Schiltz et al. ............... | 702/182 |

OTHER PUBLICATIONS

MachineView Incorporated, *SCOUT Portable Continuous Machinery Monitor and Dual–Channel FFT Analyzer*, Product Information Brochure, No Date, 4 pages.

Computational Systems Incorporated, *The Machine View System*, Product Brochure, No Date, 6 pages.

Computational Systems, Inc., *TrendSetter*, Summer 1992 (No Month), vol. 3, No. 3, pp. 1–11.

Computational Systems, Incorporated, *MACHINEVIEW; Automated Predictive Maintenance of Your Critical Plant Machinery for Improved Plant Production*, BR–S–004, Feb. 4, 1992, 7 pages.

Computational Systems, Inc., *Machineview Scout Portable System M3200*, Product Flyer, No Date, 2 pages.

Photograph, *Compaq III Computer*, (No Date).

*Be Ready for Technology Leap at the End of the Century: Three Non–ADC Developments to Springboard Automatic Data Capture Growth*, Automatic ID News, Apr. 1995.

Ikeya, PC Card Technology Primer, http://www.pcnia.org/pccard,htm, pp. 1–4, Nov. 28, 2000.

*Maintenance Products and Maintenance Matters of General Interest*, Maintenance, Jan./Feb. 1995, pp. 31–32.

Pioneer Hill Software, *Turn Your Multimedia PC into a Powerful Spectral Analysis Workstation*, Product Brochure, 14 pages (No Date).

CSL, *Wavepak an FFT Signal Analyzer Inside Your IBM PC*, Product Brochure, 6 pages (No Date).

National Instruments, *Instrumentation Reference and Catalogue*, Product Brochure 1995 (No month).

Communication Automation & Control, Inc., *PCMCIA TI TMS320C32 Bulletdsp*, Product Brochure (No Date).

SAIC, *Machineexpert Portable Data Analyzer*, Product Brochure (No Date).

Vibration Test Systems Brochure, *Plantman*™, Vibrations, vol. II, No. 2 (Jun. 1995).

MagicRAM, Inc., *PCMCIA 16–bit Audio Adapter*, Product Brochure (No Date).

Fujitsu Personal Systems, Inc., *Stylistic 500*, Product Brochure (No Date).

Industrial Monitoring Instrumentation, *QSG–200*, Product Catalog (No Date).

Entek Scientific Corporation, *Emonitor for Windows*, User's Guide (1994, no month).

Nagase Mamoru, *Vibration Measuring Apparatus*, Japanese Abstract No. JP7253352, Published Oct. 3, 1995.

* cited by examiner

PORTABLE, SELF-CONTAINED DATA COLLECTION SYSTEMS AND METHODS

CROSS-REFERENCE TO RELATED APPLICATIONS

This application is a divisional of prior application Ser. No. 09/152,429, filed on Sep. 14, 1998, now U.S. Pat. 6,411,921, which is a continuation of prior application Ser. No. 08/526,981, filed on Sep. 12, 1995, now U.S. Pat. 5,808,903.

FIELD OF THE INVENTION

This invention relates to predictive maintenance systems and methods, and more particularly to computer-based data collection systems and methods for measuring and collecting vibration data from machines.

BACKGROUND OF THE INVENTION

Data collection systems and methods are now widely used for measuring and collecting vibration data from machines, for predictive maintenance purposes. Data collection systems typically include two major components: a portable data collector and a host computer. The portable data collector is typically a dedicated instrument to which accelerometers can be coupled, and which stores accelerometer-based vibration data for a machine. An example of a state-of-the-art data collector is the EMONITOR® dataline™ data collector marketed by Entek Scientific Corporation, assignee of the present application. The EMONITOR® dataline™ data collector is described in a manual entitled *"EMONITOR® for Windows EMONITOR® dataline™ (U.S.) Data Collector User's Guide, First Edition 1995"*, Manual No. EEW2501A, published by Entek Scientific Corporation, the disclosure of which is incorporated herein by reference.

The host computer is typically a standard PC-based computer which runs predictive maintenance data management and analysis software thereon. The host software allows a user to set up a database to model the machinery for which vibration data is to be obtained. The software allows lists of machines to be set up for data collection. Each list includes a set of measurement parameters that control where and how to take and store a measurement. The host software allows one or more lists to be loaded into the data collector for collection. The user then takes the data collector to a machine to be measured, accesses the measurement parameters for that machine, and collects and stores vibration and other information. After collection, the data is unloaded from the data collector to the host. The host software then allows the data to be analyzed. Reports can be generated, including reports of measurements that exceed alarms. Graphical displays of the data can be produced, including trend, spectrum, frequency trend, time waveform and spectrum map plots.

An example of data management and analysis host software is EMONITOR® for Windows, which is marketed by Entek Scientific Corporation, the assignee of the present invention. The EMONITOR® for Windows software is described in a manual entitled *"EMONITOR® for Windows User's Guide, Second Edition 1994"*, Manual No. EEW0002B, published by Entek Scientific Corporation, the disclosure of which is incorporated herein by reference.

In state-of-the-art manufacturing environments, the capital investment in machinery can be staggering. Accordingly, there is a great need for predictive maintenance to prevent machine breakdowns and increase reliability. Moreover, with "just in time" manufacturing requirements, predictive maintenance becomes even more critical to eliminate machine down time. Accordingly, there is a great need for data collection systems and methods.

Unfortunately, the high cost of data collection systems is often a barrier to their widespread use. The high cost is in part related to the use of special purpose hardware and software in the data collector. In addition to high cost, the use of special purpose hardware and software limits the flexibility of the data collector and makes it difficult to update and improve the data collector. Although portable computers, laptop computers, pen-based computers, palmtop computers and Personal Digital Assistants (PDA) have become widely available, they have not yet made a significant impact on data collectors. See for example, the publication in Automatic ID News, April 1995, entitled *"Be Ready for Technology Leap at the End of the Century: Three Non-ADC Developments to Springboard Automatic Data Capture Growth"*. See also the publication in Maintenance, January/February 1995, by Billson et al. entitled *"Portable Pen Computers—An Essential Tool for the Mobile Maintenance Engineer"*.

SUMMARY OF THE INVENTION

The present invention is a portable, self-contained data collection system for measuring and collecting vibration data from machines. The system includes an accelerometer including a motion sensitive transducer and an accelerometer output. The accelerometer is coupled to a machine to produce an analog signal at the accelerometer output. The system also includes a data acquisition card having an analog input and a digital output. The accelerometer output is electrically coupled to the analog input. As used herein, electrical coupling includes wireless, optical or conventional wire coupling. The data acquisition card samples and digitizes the analog signal to produce a time domain digital signal, i.e. a sampled and digitized series of voltage versus time points, at the digital output. The system also includes a battery-powered portable computer such as a pen-based computer, which includes an expansion slot. The data acquisition card digital output is electrically and mechanically connected to the expansion slot.

The battery-powered portable computer also includes a database having machine identifications and associated measurement parameters. User input means such as a pen allows user selection of a machine identification for measurement. The portable computer also includes signal processing means for processing the time domain digital signal according to the measurement parameters associated with the selected machine identification. Preferably, the signal processing means processes the time domain digital signal to produce a frequency domain digital signal by performing a Fast Fourier Transform (FFT), wavelet or other digital signal processing operations. Finally, the battery-powered portable computer also preferably includes signal analyzing means for analyzing the frequency domain digital signal to produce predictive maintenance information such as spectral distribution. The time domain digital signal can also be analyzed to produce crest factor and other predictive maintenance information.

A data collection system according to the present invention uses a standard portable computer such as a pen-based computer and a standard data acquisition card such as a PCMCIA sound card, to provide portable self-contained hardware for data collection and analysis. The machine database, signal processing means and signal analyzing means are preferably implemented using software modules which execute on the portable computer. The machine database and the signal analyzing software may be provided using EMONITOR® for Windows or other predictive maintenance software on the portable computer. Signal processing software may be provided by conventional digital signal processing software which provides digital filtering, integration from acceleration to velocity or displacement units, Fast Fourier Transform or other mathematical functions, and averaging. Accordingly, a low cost self-contained data collection system is provided.

It will be understood that since the portable data collection system includes a database, signal processing software and signal analyzing software therein, a host computer connection is not required for operation. Rather, all predictive maintenance operations may be performed using only the portable self-contained data collection system. However, it will also be understood by those having skill in the art that the portable self-contained data collection system can be used as part of a networked data collection system wherein the portable computer includes transmitting means for transmitting at least one of the machine identifications, the measurement parameters, the time domain digital signal, the frequency domain digital signal or the predictive maintenance information to a second computer. The second computer may store this data for distribution to other users and the second computer or other users may also perform one or more of the processing functions of the portable data collector. The transmitting means is preferably wireless, such as a radio frequency (RF) transmitter. However, transmission may also be accomplished by uploading information to another computer using conventional wire communications.

According to another aspect of the present invention, the portable self-contained data collection system also includes a power supply for supplying power to the accelerometer. In particular, conventional portable computers do not provide sufficient power for an accelerometer, which typically requires 24V at 2 mA. According to the invention, an accelerometer power supply electrically and mechanically couples the accelerometer output to the data acquisition card analog input. The accelerometer power supply is preferably responsive to the data acquisition card for supplying power to the accelerometer when the data acquisition card is activated, and for deactivating when the data acquisition card is deactivated.

In particular, the accelerometer power supply includes a power supply housing and an accelerometer battery power supply in the power supply housing which provides sufficient power for an accelerometer. Output means including an output connector electrically and mechanically connects the accelerometer battery power supply to an accelerometer and receives accelerometer signals from the accelerometer. Input means including an input connector electrically and mechanically connects the accelerometer battery power supply to an external device, preferably the analog input of a data acquisition card. The input means receives a control signal from the external device, and also passes the accelerometer signals to the external device. The accelerometer battery power supply is responsive to the control signal, to activate the accelerometer battery power supply to supply battery power for an accelerometer to the output connector. In the absence of the control signal, the accelerometer battery power supply is deactivated. Preferably, the accelerometer battery power supply will pass signals from the output means to the external device in the absence of the control signal, so that non-powered transducers can be used.

When the accelerometer power supply is included, the portable self-contained data collection system includes three hardware components: a portable computer, a data acquisition card and an accelerometer power supply. The portable computer includes a portable computer housing, a portable computer battery power supply within the portable computer housing to supply power to the portable computer, and an expansion slot in the portable computer housing. The data acquisition card is mechanically and electrically coupled to the expansion slot. The accelerometer power supply includes a power supply housing, and an accelerometer battery power supply within the power supply housing which provides sufficient power for an accelerometer. The accelerometer power supply is electrically and mechanically coupled to the data acquisition card and the accelerometer is electrically and mechanically coupled to the accelerometer power supply. The portable computer, data acquisition card and accelerometer power supply may be packaged in a ruggedized carrying case. The portable computer executes software including a database including machine identifications and measurement parameters, signal processing software for processing accelerometer signals and signal analyzing software for analyzing the processed signal to produce predictive maintenance information.

Data collection methods according to the present invention are used for measuring and collecting vibration data from machines, wherein the following steps are all performed in a portable battery-powered computer: A machine identification for measurement is selected. A time domain accelerometer signal is processed according to measurement parameters associated with the selected machine identification to produce a digital signal. The digital signal is analyzed to produce predictive maintenance information. If necessary, the processing step is preceded by the step of sampling and digitizing an analog accelerometer signal to produce the time domain accelerometer signal. The machine identifications, measurements, time domain signal, digital signal and/or predictive maintenance information can be displayed on the portable battery-powered computer. Portable self-contained data collection systems and methods are thereby provided. In addition, this information can be transferred to another computer.

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
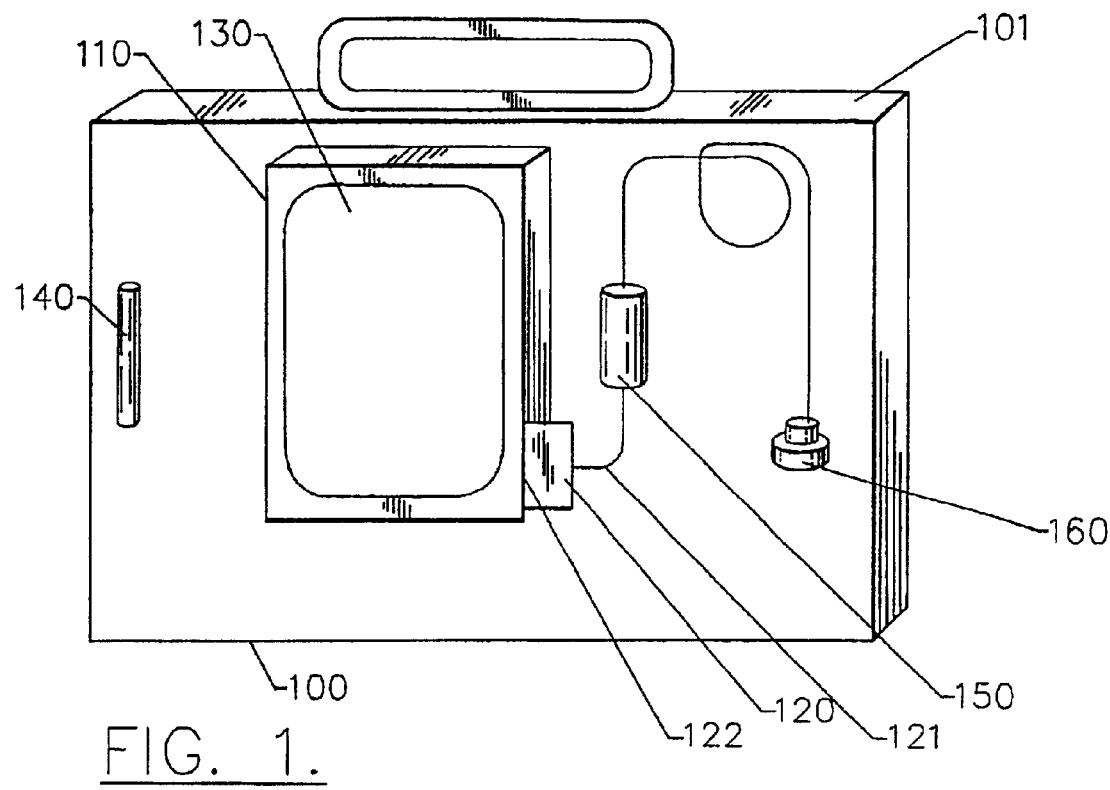
FIG. 1 illustrates a data collection system for collecting vibration data from machines according to the present invention.

Referring now to FIG. 1, data collection system 100 is illustrated, housed in a case 101. As shown, data collection system 100 includes a battery-powered portable computer 110 mating to data acquisition card 120, display means 130, user input means 140, power supply 150, and accelerometer 160.

The construction of battery powered portable computer 110 is well-known to those skilled in the art. Battery operated portable computers typically include a microprocessor, associated random access memory (RAM), nonvolatile data storage such as a hard disk drive, a battery power source and expansion slots designed to accommodate circuit boards electrically coupling the computer components to external devices such as keyboards, pens, mouses, transducers and displays. These expansion slots typically accommodate standard form factor circuit cards, such as the industry-standard PCMCIA form factor cards used in notebook and laptop computers. For field uses, such as monitoring of machinery for predictive maintenance purposes, battery operated portable computer 110 may be mounted in a lightweight, rugged hand-held case 101, and user input means 140 may include a magnetic pen designed to operate with a magnetically sensitive screen matrix. An example of a typical battery operated portable computer designed especially for field use is the Fujitsu Stylistic 500, as described in Fujitsu brochure 58-0349-00B, the disclosure of which is incorporated herein by reference. This computer is referred to for purposes of explanation only, and it will be understood by those skilled in the art that the present invention may be used with other portable computers.

Data acquisition card 120 is an analog to digital (A/D) converter card that mechanically and electrically couples data acquisition card 120 to an expansion slot in battery powered portable computer 110, electrically connecting digital output 122 to battery operated portable computer 110. Data acquisition card 120 is electrically coupled to accelerometer 160 at analog input 121. Typically, data acquisition card 120 is a low-cost standard form factor sound card designed to receive audio frequency analog signals at analog input 121. An example of such a sound card is the Magic Ram PCMCIA 16-bit audio adapter, which is described in a manufacturer's data sheet entitled "PCMCIA 16-bit Audio Adapter," the disclosure of which is incorporated herein by reference. This device is a standard PCMCIA form factor card that mates with a PCMCIA expansion slot. It will be understood by those skilled in the art that a data acquisition card according to the present invention includes any A/D converter card capable of receiving analog inputs and transmitting corresponding digital signals to a battery operated portable computer through a digital communications port, such as an expansion slot. It will also be understood by those skilled in the art that the present invention may be used with a battery operated portable computer 110 which includes an analog input and associated internal A/D.

Accelerometer 160 produces an analog signal corresponding to the accelerations experienced by a motion sensitive transducer included therein, and is electrically coupled to data acquisition card 120 by analog input 121. The motion-sensitive transducer is typically piezoelectric and produces a voltage proportional to the acceleration of the transducer. The accelerometer includes means for coupling the motion sensitive transducer to a machine from which the user desires vibration data, such as a probe extension, screw or magnet attached to the accelerometer structure. Examples of piezoelectric accelerometers may be found in Catalog QSG-200, published by Industrial Monitoring Instrumentation Division of PCB Piezotronics, Inc., the disclosure of which is incorporated herein by reference. It will be understood by those skilled in the art that the present invention may be used with other measurement devices producing analog output signals corresponding to accelerations, such as piezotransistor or variable resistance accelerometers.

Power supply 150 supplies electrical power to accelerometer 160, receives output signals from accelerometer 160, receives control signals from data acquisition card 120, and conveys output signals from accelerometer 160 to data acquisition card 120. Power supply 150 is mechanically and electrically coupled to both accelerometer 160 and data acquisition card 120.

Figure 2:
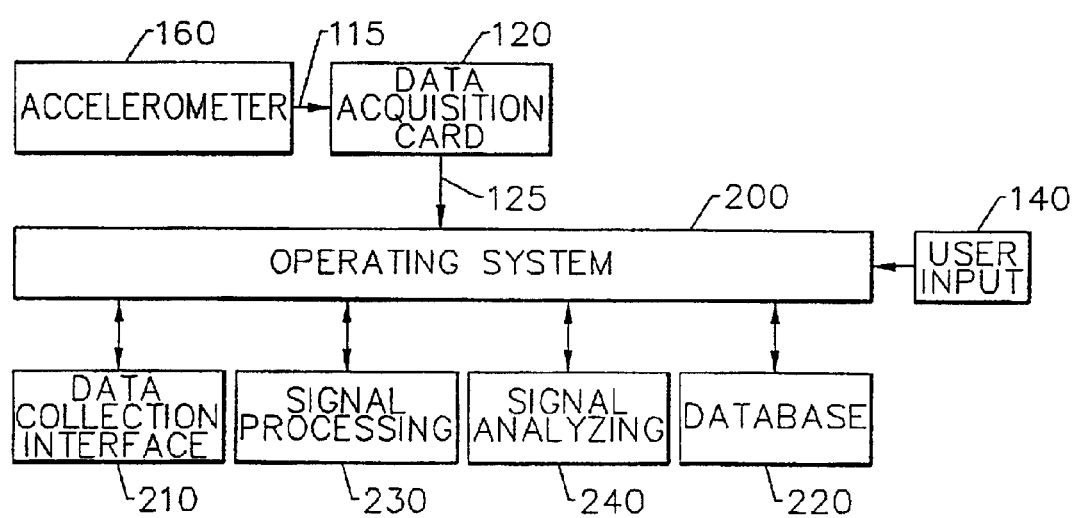
FIG. 2 is a block diagram illustrating a data acquisition card interfaced to an operating system, database, signal processing means and signal analyzing means implemented in a battery operated portable computer according to the present invention.

Referring now to FIG. 2, a block diagram illustrates accelerometer 160, data acquisition card 120 and user input means 140 interfaced to an operating system 200, data collection interface 210, database 220, signal processing means 230 and signal analyzing means 240. Operating system 210 is typically executive software that controls data collection interface 210, database 220, signal processing means 230, signal analyzing means 240, and data acquisition card 120, responsive to commands received through user input means 140. Such commands may be to acquire or store data, or to perform filtering, time domain analysis, or frequency domain analysis. An example of operating system 200 is Entek Scientific Corporation's EMONITOR® for Windows data management software, as described in "EMONITOR® for Windows User's Guide, Second Edition 1994," Manual No. EEW0002B, the disclosure of which is incorporated herein by reference. This software is a Windows-based program that enables a user to perform database manipulation, data analysis or other operations via manipulation of screen icons. It will be understood by those skilled in the art that the present invention may be used, for example, with other operating systems running in a Windows, DOS, or UNIX environment.

Database 220 comprises a plurality of machine identifications and associated measurement parameters. Database 220 may have a hierarchical, relational or other structure and is typically organized according to logical relationships between particular machines. An example of a hierarchical database structure is incorporated in Entek Scientific Corporation's EMONITOR® for Windows, as described in Chapters 4 and 5 of "EMONITOR® for Windows User's Guide, Second Edition 1994," Manual No. EEW0002D. This database is a SQL database that organizes machine identifications, and associates parameters such as machine location, signal processing parameters and previously measured data values with these machine identifications. This database is referred to for purposes of explanation, and it will be understood by those skilled in the art that the present invention may be used with other hierarchical or non-hierarchical database structures, and may include various combinations of machine parameters.

Data collection interface 210 is preferably a software module that controls the operation of data acquisition card 120 and signal processing means 230 through operating system 200, although hardware or software/hardware combinations may be employed. Upon commands from data collection interface 210, data acquisition card 120 samples and digitizes an analog signal 115 received from a accelerometer 160 and provides a corresponding time domain digital signal 125, which is conveyed to signal processing means 230. In the embodiment of the present invention shown in FIG. 2, data collection interface 210 is a software module operating in conjunction with, for example, an operating system such as EMONITOR® for Windows running in a Windows environment, and is conveniently accessed and controlled by user selection of appropriate icons in a display window.

Although the combination of elements described in FIG. 2 envisions data collection, database management and data analysis integrated in a multitasking environment such as Windows, it will be understood by those skilled in the art that the present invention may be practiced using other means of interfacing data acquisition card 120, signal processing means 230, signal analyzing means 240 and database 220. For example, data collection interface 210 may be a standalone software program capable of transferring data from data acquisition card 120 to database 220 for subsequent data management, signal processing and signal analysis. In another arrangement, data acquisition card 120 may include all or a portion of signal processing means 230, allowing sampling, digitizing and processing of analog signal 115 to be performed on data acquisition card 120. An example of such an integrated PCMCIA card is the Bullet$_{dsp}$ card marketed by Communication Automation and Control, Inc. The Bullet$_{dsp}$ card is described in a data sheet entitled "*PCMCIA TI TMS320C32*," published by Communication Automation and Control, Inc., the disclosure of which is incorporated herein by reference.

Signal processing means 230 performs digital signal processing of time domain digital signal 125 received from data acquisition card 120. Typically, signal processing means 230 is implemented in conventional modular software blocks, which may be selected and combined to perform various processing functions, as further illustrated in FIG. 3. This software may implement functions such as filtering, fast Fourier transform, integration or averaging, which may be selected and arranged as desired.

Signal analyzing means 240 typically is software that examines processed digital signals received from signal processing means 230 and produces predictive maintenance information. Upon commands received through operating system 200, signal analyzing means 240 conducts analyses such as trend analysis, alarm detection, spectral analysis, data plotting or report generation. An example of signal analyzing means 240 is the analysis software incorporated in Entek Scientific Corporation's EMONITOR® for Windows, as described in Chapters 7, 9, 10 and 11 of "EMONITOR® for Windows User's Guide, Second Edition 1994," Manual No. EEW0002B.

Figure 3:
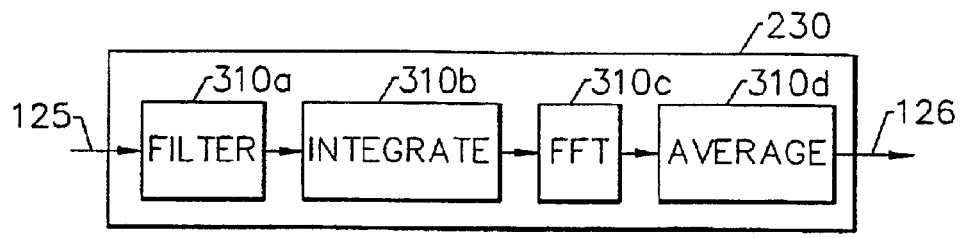
FIG. 3 is a block diagram illustrating signal processing means, including filtering, integration, fast Fourier transform, and averaging, for processing a time domain digital signal according to the present invention.

Referring now to FIG. 3, a software block diagram illustrates signal processing software for implementing signal processing means 230 which includes modular processing elements 310a–310d which may be selected and combined as required. It will be understood by those skilled in the art that other arrangements of signal processing elements may be used with the present invention. In addition, it will be understood by those skilled in the art that other non-modular signal processing software techniques may be used with the present invention.

Figure 4:
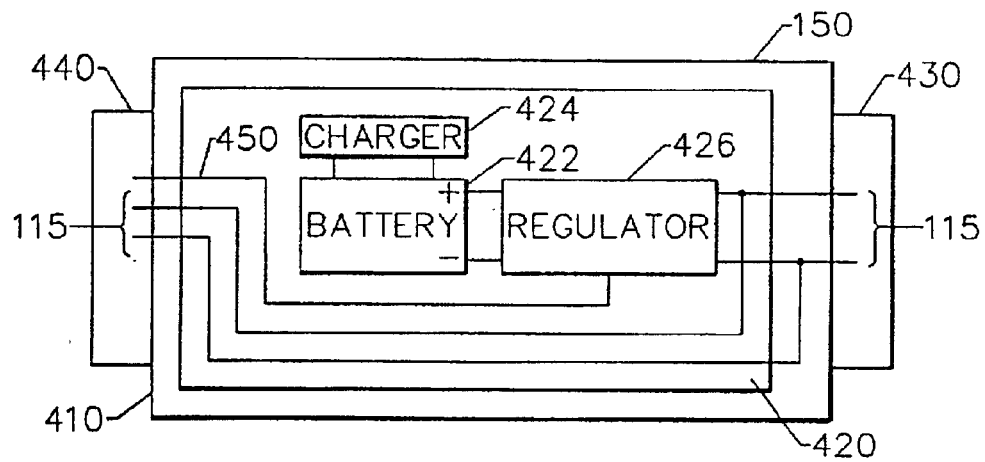
FIG. 4 is a block diagram illustrating a power supply for an accelerometer according to the present invention.

Referring now to FIG. 4, an electrical block diagram illustrates power supply 150 for accelerometer 160. Power supply housing 410 encloses accelerometer battery power supply 420. Accelerometer battery power supply 420 provides sufficient power to excite an external accelerometer. Output means 430 electrically and mechanically couples accelerometer battery power supply 420 to an external accelerometer. Typically, output means 430 will include an MS-3106 connector commonly used in accelerometer applications, but it will be understood by those skilled in the art that other structures may be used with the present invention, including coaxial and other types of standard connectors.

Input means 440 electrically and mechanically couples accelerometer battery power supply 420 to an external device, such as an A/D converter, and receives control signal 450 from the external device. Accelerometer battery power supply 420 may be responsive to control signal 450, deactivating power output to the external accelerometer in the absence of control signal 450, thus offering the capability to minimize power consumption during non-measurement periods and extending battery life or time between recharges.

FIG. 4 shows accelerometer battery power supply 420 further including battery 422, charging means 424, and regulating means 426. Charging means 424 provides the capability to charge battery 422. Regulating means 426 takes the power output from battery 422 and provides the voltage and current conditioning required to excite the external accelerometer. It will be understood by those skilled in the art that not all of these elements are required for all embodiments of the present invention. Different power supply configurations may, for example, utilize disposable or removable batteries and eliminate the need for internal charging means 424.

Figure 5A:
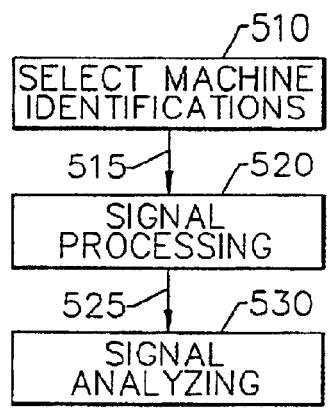
FIGS. 5a, 5b, 5c, 5d and 5e illustrate data collection operations according to the present invention.
Figure 5B:
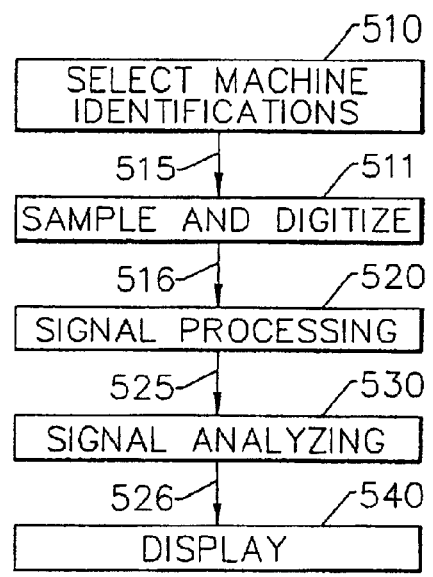

FIG. 5a illustrates operations for measuring and collecting vibration data from machines, implemented in a battery-operated powered computer. First, in Block 510 a user selects a machine identification for measurement. In Block 520 a time domain accelerometer signal 515 is processed to produce a digital signal 525. In Block 530 the digital signal is analyzed to produce predictive maintenance information, such as detection of alarm conditions due to vibration magnitudes exceeding predetermined limits or reports concerning machine vibration parameters. Referring to FIG. 5b, in an alternate embodiment, the operations of Block 520 may be preceded by a step of sampling and digitizing an analog time domain accelerometer signal to produce a time domain digital accelerometer signal 516, as shown in Block 511. In addition, predictive maintenance information 526 may then be displayed, as shown in Block 540.

Figure 5C:
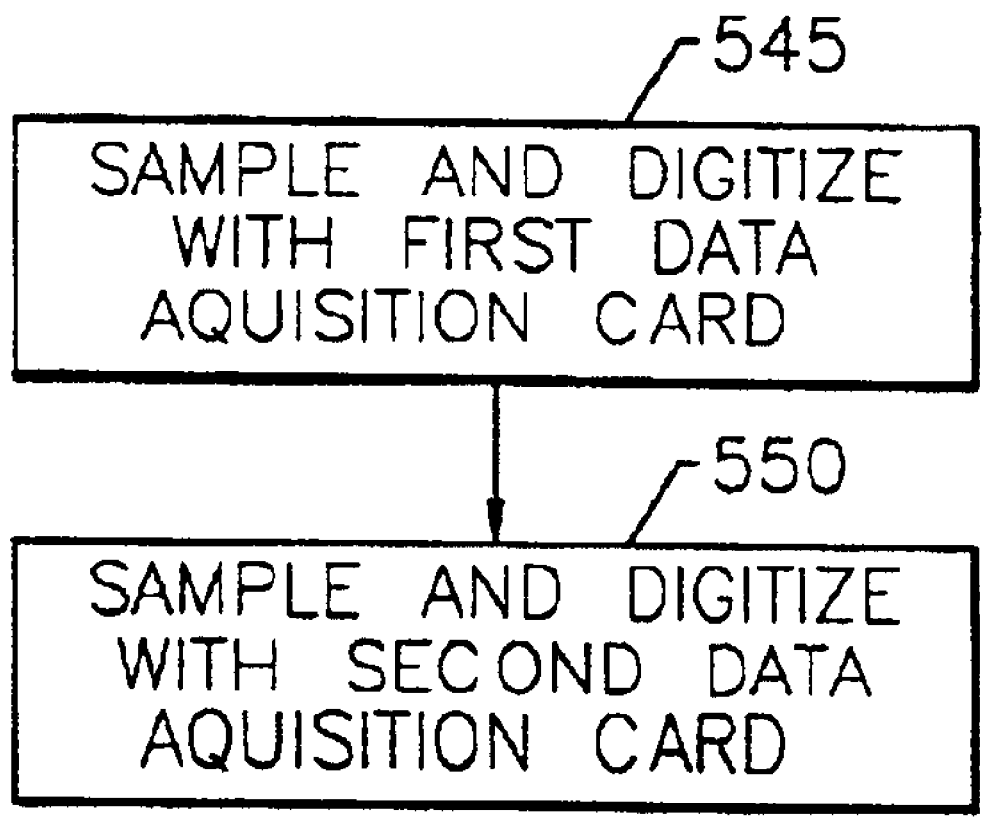

Referring to FIG. 5c, the operations of block 511, of sampling and digitizing an analog time domain accelerometer signal, to produce a time domain digital accelerometer signal 516, may be performed using the different data acquisition cards 120, such as the Magic Ram PCMCIA 16-bit audio adapter identified above or the Bullet$_{dsp}$ PCMCIA card identified above. Because data acquisition card 120 is removable, the cards may be exchanged for use in different measurements. Specifically, a first card may be used in block 545 for a first sampling operation and a second card may be used in block 550 for a second sampling operation.

Figure 5D:
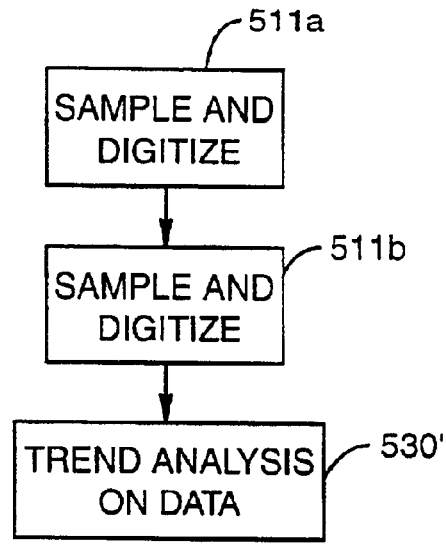

Referring to FIG. 5d, the operations involved in trend analysis, as discussed above, are detailed. Specifically, in a first sample and digitize step 511a, analog time domain accelerometer signals are converted to a digital time domain accelerometer signals. Similarly, in a second, later performance of a sample and digitize step 511b, analog time domain accelerometer signals collected at that time are converted to a digital time domain accelerometer signals. Finally, signal analysis 530, in the form of a trend analysis 530', is performed, to identify changes between the first and second stored digital signal created in steps 511a and 511b, respectively.

Figure 5E:
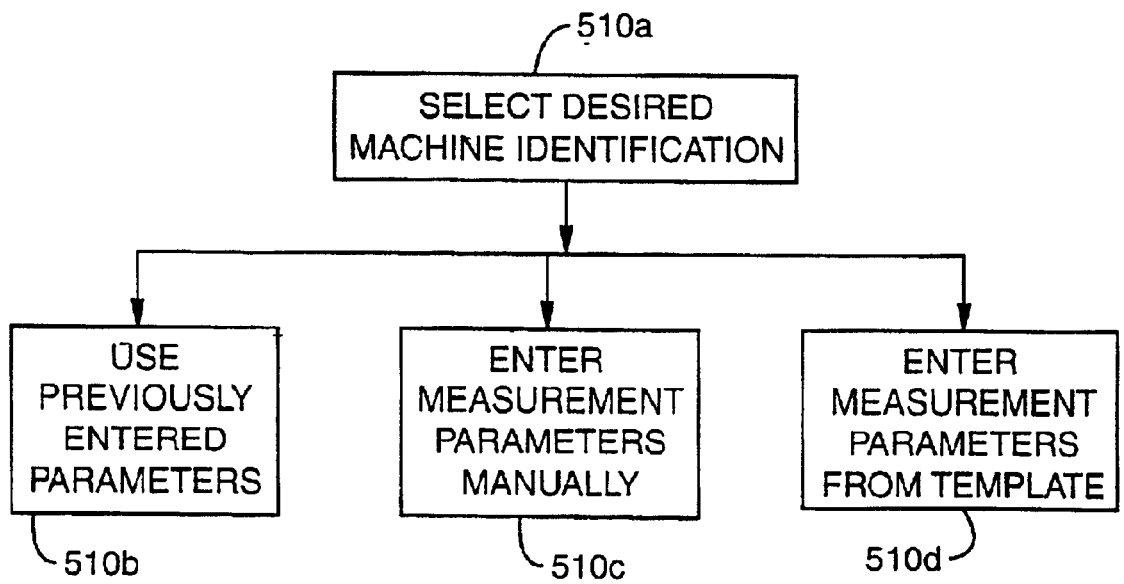

Referring to FIG. 5e, step 510 of FIG. 5a, of selecting a machine identification, is detailed. A machine identification and associated parameters are selected (510a) in one of three ways. An identification and associated previously stored parameters may be selected in step 510b. Alternatively, a machine identification and parameters may be entered manually in step 510c (see FIG. 6b, below). As a further alternative, parameters may be entered with the aid of predetermined machine templates in step 510d (see FIG. 6c, below).

Figure 6A:
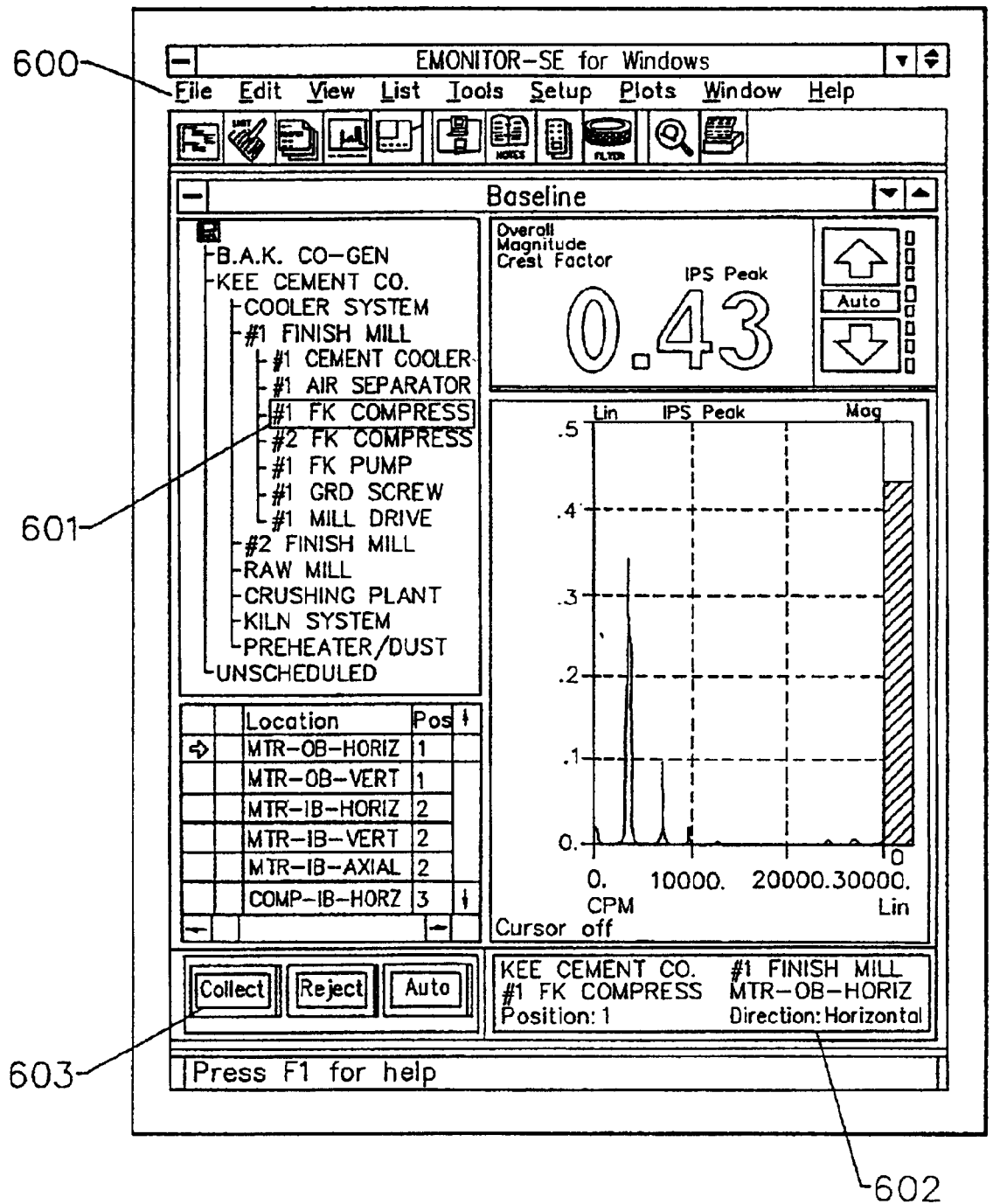
FIGS. 6a–6c are computer screen images illustrating a machine identification selection according to the present invention.
Figure 6B:
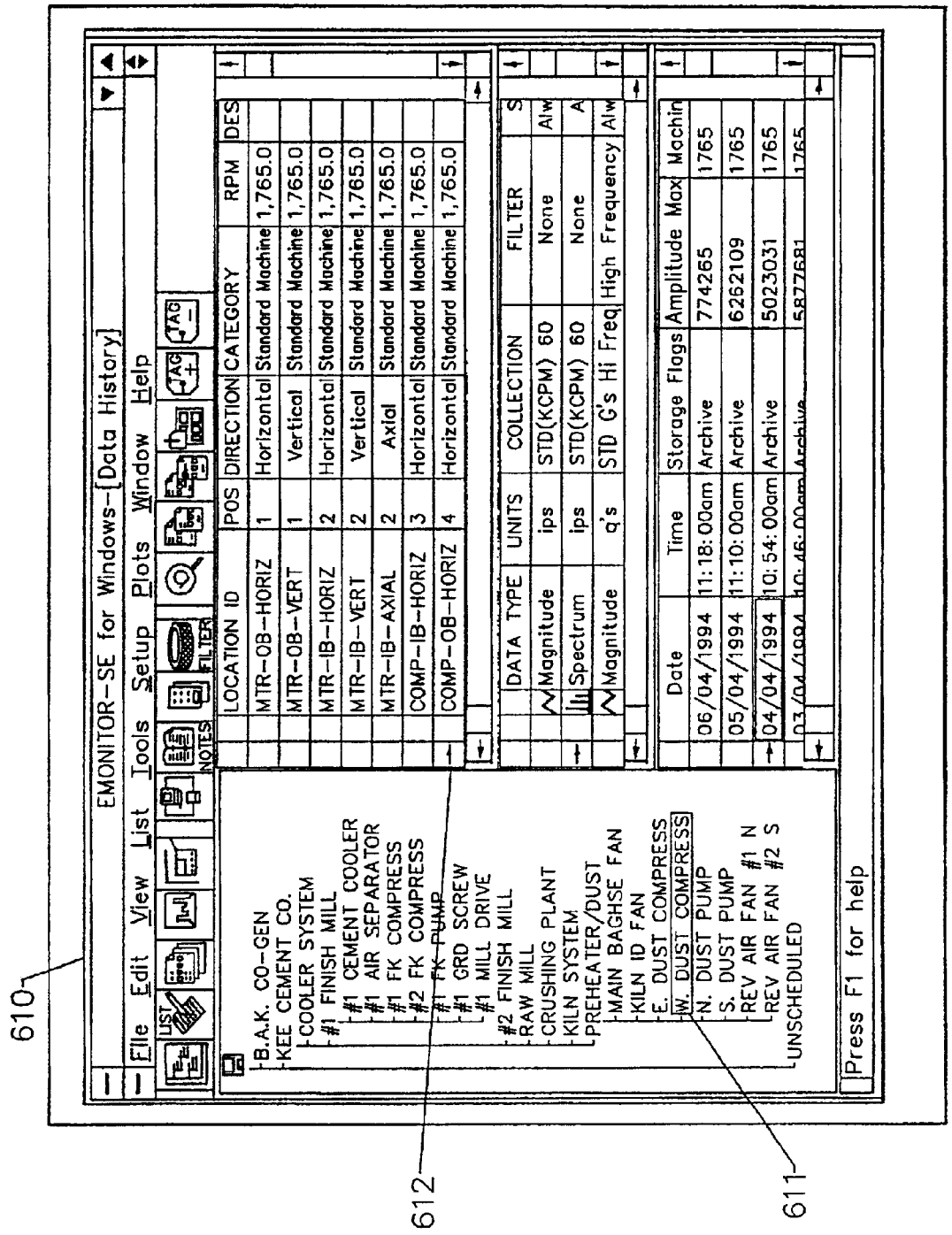

FIGS. 6a–6b illustrate the selection step of Block 510 of FIGS. 5a–5b in greater detail. In FIG. 6a the user enters a data collection window 600 in which he may select a machine identification for measurement, as shown at 601. The display informs the user of the identification selected, which typically is a location on a particular machine, as shown at 602. The user typically commands data acquisition by selection of an icon, as shown at 603.

Figure 6C:
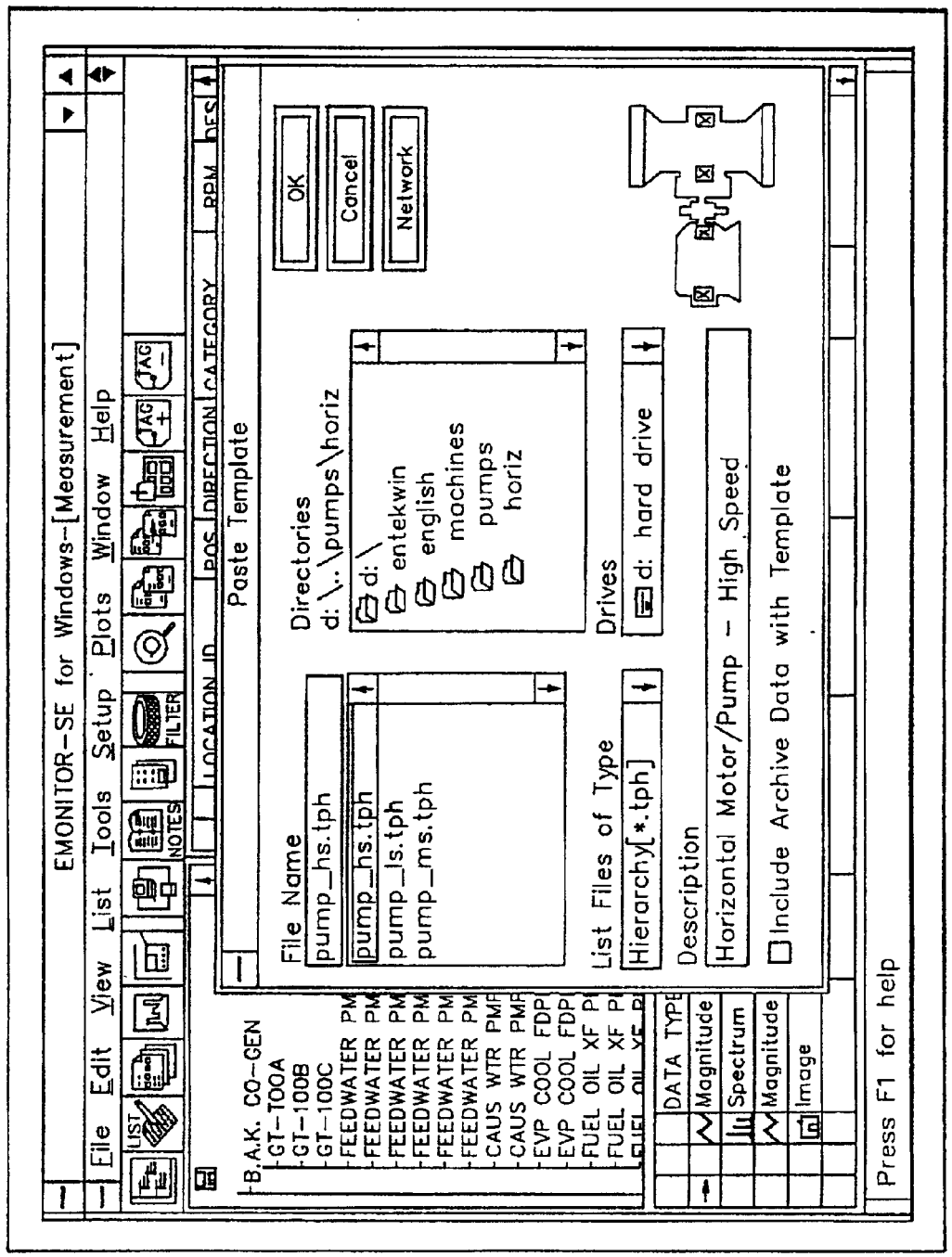

The parameters associated with a particular machine identification typically have been previously entered into a database. This may be done manually, as shown in FIG. 6b. Within a data entry window 610, the user selects a desired machine identification, as illustrated at 611, and enters the associated parameters, as shown at 612. Alternatively, parameters may be entered with the aid of predetermined machine templates, as shown in FIG. 6c. These parameters may include signal processing parameters for use in the processing step of Block 520 of FIG. 5, but it will be understood by those skilled in art that other arrangements may be used with the present invention, such as allowing the user to select particular signal processing parameters while in data collection window 600.

Figure 7:
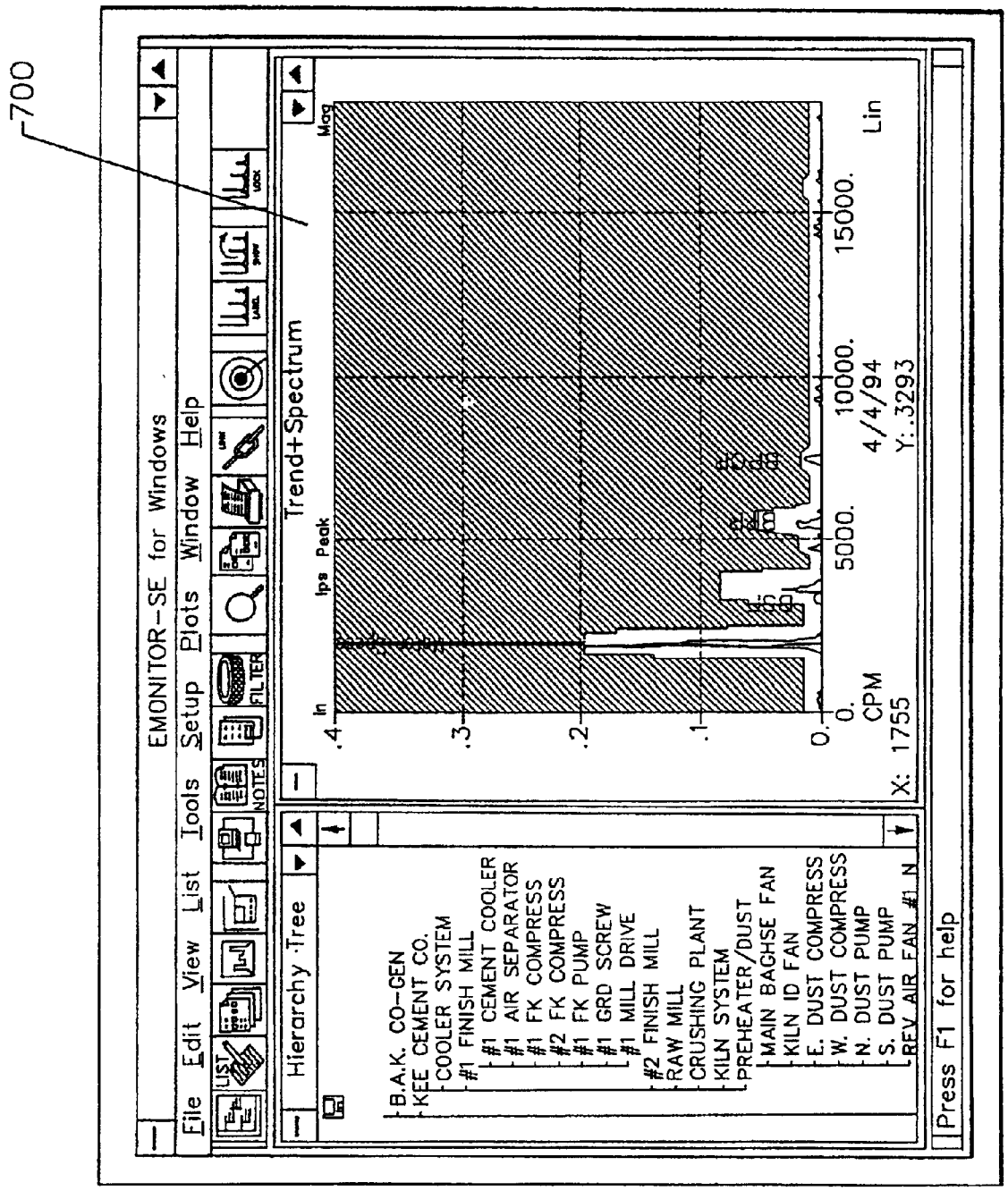
FIG. 7 is a computer screen image illustrating signal analyzing according to the present invention.

FIG. 7 illustrates the signal analyzing operation of Block 530 of FIG. 5, specifically the displayed results of a spectrum analysis. It will be understood by those skilled in the art that other analyses may be performed on digital signals, such as magnitude or crest factor calculations or detection of alarm conditions.

Figure 8:
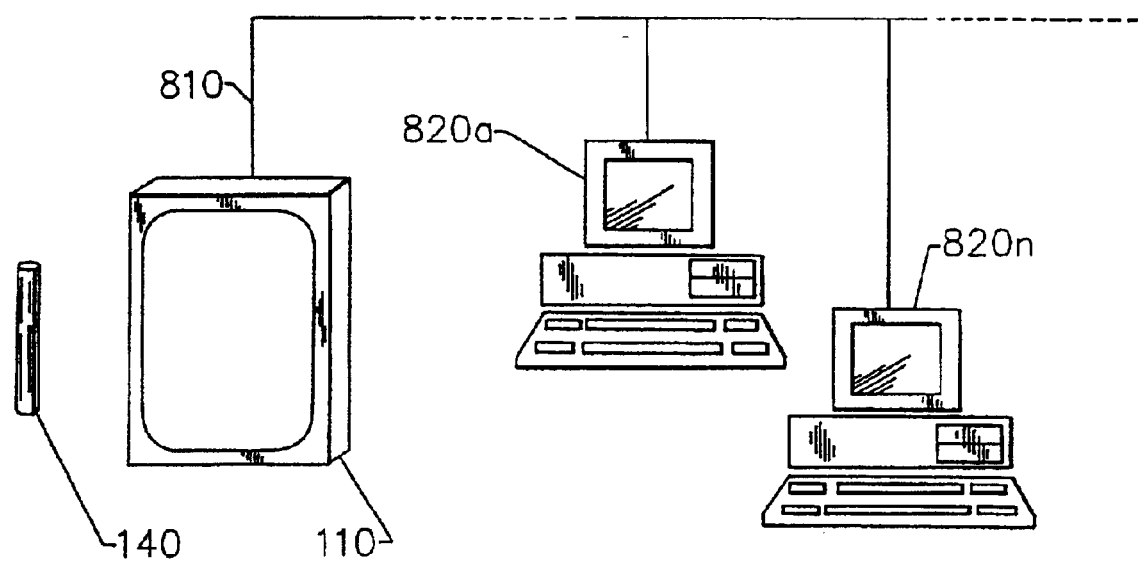
FIG. 8 is a diagram illustrating a data collection system implemented in a battery operated portable computer linked to other computers in a computer network according to the present invention.

FIG. 8 illustrates the data collection system of the present invention further including transmission of machine identifications, measurement parameters, time domain accelerometer signals, frequency domain digital signals and predictive maintenance information to other computers 820a–820n linked to the battery operated portable computer 110 by means of a network 810. It will be understood by those skilled in the art that network 810 may be hardwired or may employ radio frequency (RF) or other communications links. Under this aspect of the invention, machine-related data may be uploaded from the battery powered portable computer 110 to computers 820a–820n for subsequent data management, processing, analysis or display.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method of collecting machinery maintenance data from machines, comprising:

providing a portable computer comprising a processor, memory, battery, and external interface, providing an analog machine activity sensor for collecting machinery maintenance data from one or more machines, during battery-powered operation of said portable computer, collecting first data relating to operation of a machine at a first time, from said analog machine activity sensor, via said external interface, into said memory of said portable computer, during battery-powered operation of said portable computer, collecting second data relating to operation of said machine at a second time separate from said first time, from said analog machine activity sensor, via said external interface, into said memory of said portable computer, and retrieving said first and second data from said memory of said portable computer to said processor of said portable computer and using said processor to analyze said first and second data by comparing said first and second data for changes indicative of machinery maintenance needs.

2. The method of claim 1 wherein said memory comprises dynamic random access memory (DRAM).

3. The method of claim 1 wherein said memory comprises magnetic storage.

4. The method of claim 1 wherein said memory is removable.

5. The method of claim 1 wherein said external interface is a card slot, and an interface card inserted therein, both compatible with a personal computer interface standard permitting removal and replacement of said interface card without restarting operation of said processor.

6. The method of claim 5 wherein said interface card comprises an analog to digital converter.

7. The method of claim 1 wherein analyzing said first and second data comprises operating said processor to perform a frequency transformation of said first and/or second data.

8. The method of claim 1 further comprising providing a sensor power supply for supplying power to said analog machine activity sensor.

9. The method of claim 8 wherein said sensor power supply is responsive to a control signal from said portable computer to activate or deactivate said analog machine activity sensor, and further comprising operating said portable computer to produce a control signal to activate said sensor power supply prior to collecting data from said analog machine activity sensor.

10. The method of claim 8 further comprising providing an interface cord connecting said sensor power supply and said analog machine activity sensor to said portable computer.

11. The method of claim 8 wherein said sensor power supply comprises a sensor power supply battery, and further comprising providing a battery charger and connecting said battery charger to said sensor power supply battery to charge said sensor power supply battery.

12. The method of claim 1 further comprising storing in said memory machine identifications and associated measurement parameters for a plurality of machines.

13. The method of claim 12 wherein said portable computer further comprises a connector for transmitting information between said memory and a host computer.

14. The method of claim 13 further comprising transmitting at least one of data collected from
said analog machine activity sensor,
an identification of a machine, and
measurement parameters between said memory and said host computer via said connector.

15. The method of claim 12 wherein said portable computer further comprises a user interface, and further comprising interacting with said processor using said user interface to select a machine identification, and then processing data collected from said analog machine activity sensor in accordance with measurement parameters associated with said selected machine identification.

16. The method of claim 1 wherein said portable computer further comprises a display.

17. The method of claim 16 further comprising operating said processor to display data collected from said analog machine activity sensor on said display.

18. The method of claim 16 further comprising operating said processor to perform a frequency transformation of data collected from said analog machine activity sensor and display said frequency transformation on said display.

19. The method of claim 1 wherein said portable computer has less than a full set of alphanumeric keys.

20. The method of claim 19 wherein said portable computer is a pen-based palmtop computer.

21. The method of claim 1 wherein said analog machine activity sensor is an accelerometer.

22. A computer system for collecting machinery maintenance data from machines, comprising:
a portable computer comprising a processor, memory, battery, external interface, and user interface, said user interface having less than a full set of alphanumeric keys,
software in said memory for operating said processor to collect first and second data relating to operation of a machine at first and second separated times, from an analog machine activity sensor connected to said external interface, and store said first and second data into said memory of said portable computer, and
software in said memory for operating said processor to retrieve said first and second data collected from said single machine from said memory of said portable computer to said processor of said portable computer and use said processor to analyze said first and second data by comparing said first and second data for changes indicative of machinery maintenance needs.

23. The computer system of claim 22 wherein said memory comprises dynamic random access memory (DRAM).

24. The computer system of claim 22 wherein said memory comprises magnetic storage.

25. The computer system of claim 22 wherein said memory is removable.

26. The computer system of claim 22 wherein said external interface is a card slot, and an interface card inserted therein, both compatible with a personal computer interface standard permitting removal and replacement of said interface card without restarting operation of said processor.

27. The computer system of claim 26 wherein said interface card comprises an analog to digital converter.

28. The computer system of claim 22 wherein said software operates said processor to perform a frequency transformation of said first and/or second data.

29. The computer system of claim 22 further comprising a sensor power supply for supplying power to said analog machine activity sensor.

30. The computer system of claim 29 wherein said sensor power supply is responsive to a control signal from said portable computer to activate or deactivate said analog machine activity sensor, and further comprising software in said memory for operating said portable computer to produce a control signal to activate said sensor power supply prior to collecting data from said analog machine activity sensor.

31. The computer system of claim 29 further comprising an interface cord connecting said sensor power supply and said analog machine activity sensor to said portable computer.

32. The computer system of claim 29 wherein said sensor power supply comprises a sensor power supply battery, and further comprising a battery charger connectable to said sensor power supply battery to charge said sensor power supply battery.

33. The computer system of claim 22 further comprising machine identifications and associated measurement parameters for a plurality of machines stored in said memory.

34. The computer system of claim 33 further comprising a connector for transmitting information between said memory and a host computer, including at least one of
data collected from said analog machine activity sensor,
an identification of a machine, and
measurement parameters.

35. The computer system of claim 33 further comprising software in said memory for operating said processor to interact with a user to select a machine identification, and then process data collected from said analog machine activity sensor in accordance with measurement parameters associated with said selected machine identification.

36. The computer system of claim 22 wherein said portable computer further comprises a display.

37. The computer system of claim 36 further comprising software in said memory for operating said processor to display data collected from said analog machine activity sensor on said display.

38. The computer system of claim 36 further comprising software in said memory for operating said processor to perform a frequency transformation of data collected from said analog machine activity sensor and display said frequency transformation on said display.

39. The computer system of claim 22 wherein said portable computer is a pen-based palmtop computer.

40. A computer system for collecting machinery maintenance data from machines, comprising:
a portable computer comprising a processor, memory, battery, and external interface,
an analog machine activity sensor for collecting machinery maintenance data from one or more machines,
software in said memory for operating said processor, during battery-powered operation thereof, to collect first and second data relating to operation of a machine at first and second separated times, from said analog machine activity sensor, via said external interface, and store said first and second data into said memory,
software in said memory for operating said processor to retrieve said first and second data from said memory to said processor and analyze said first and second data by comparing said first and second data for changes indicative of machinery maintenance needs.

41. The computer system of claim 40 wherein said memory comprises dynamic random access memory (DRAM).

42. The computer system of claim 40 wherein said memory comprises magnetic storage.

43. The computer system of claim 40 wherein said memory is removable.

44. The computer system of claim 40 wherein said external interface is a card slot, and an interface card inserted therein, both compatible with a personal computer interface standard permitting removal and replacement of said interface card without restarting operation of said processor.

45. The computer system of claim 44 wherein said interface card comprises an analog to digital converter.

46. The computer system of claim 40 wherein said software further operates said processor to analyze said first and second data by operating said processor to perform a frequency transformation of said first and/or second data.

47. The computer system of claim 40 further comprising a sensor power supply for supplying power to said analog machine activity sensor.

48. The computer system of claim 47 wherein said sensor power supply is responsive to a control signal from said portable computer to activate or deactivate said analog machine activity sensor, and wherein said portable computer comprises software operating said processor to produce a control signal to activate said sensor power supply prior to collecting data from said analog machine activity sensor.

49. The computer system of claim 47 further comprising an interface cord connecting said sensor power supply and said analog machine activity sensor to said portable computer.

50. The computer system of claim 47 wherein said sensor power supply comprises a sensor power supply battery, and further comprising a battery charger connectable to said sensor power supply battery to charge said sensor power supply battery.

51. The computer system of claim 40 wherein said memory stores machine identifications and associated measurement parameters for a plurality of machines.

52. The computer system of claim 51 wherein said portable computer further comprises a connector for transmitting information between said memory and a host computer.

53. The computer system of claim 52 further comprising software operating said processor to transmit at least one of data collected from
    said analog machine activity sensor,
    an identification of a machine, and
    measurement parameters between said memory and said host computer via said connector.

54. The computer system of claim 51 wherein said portable computer further comprises a user interface, and software operating said processor using said user interface to select a machine identification, and then process data collected from said analog machine activity sensor in accordance with measurement parameters associated with said selected machine identification.

55. The computer system of claim 40 wherein said portable computer further comprises a display.

56. The computer system of claim 55 further comprising software operating said processor to display data collected from said analog machine activity sensor on said display.

57. The computer system of claim 55 further comprising software operating said processor to perform a frequency transformation of data collected from said analog machine activity sensor and display said frequency transformation on said display.

58. The computer system of claim 40 wherein said portable computer has less than a full set of alphanumeric keys.

59. The computer system of claim 58 wherein said portable computer is a pen-based palmtop computer.

60. The computer system of claim 40 wherein said analog machine activity sensor is an accelerometer.

61. A method for collecting machinery maintenance data from machines, comprising:
    providing a portable computer comprising a processor, memory, battery, external interface, and user interface, said user interface having less than a full set of alphanumeric keys,
    operating said processor to collect first and second data relating to operation of a machine at first and second separated times, from an analog machine activity sensor connected to said external interface, and store said first and second data into said memory of said portable computer, and
    operating said processor to retrieve said first and second data collected from said single machine from said memory of said portable computer to said processor of said portable computer and use said processor to analyze said first and second data by comparing said first and second data for changes indicative of machinery maintenance needs.

62. The method of claim 61 wherein said memory comprises dynamic random access memory (DRAM).

63. The method of claim 61 wherein said memory comprises magnetic storage.

64. The method of claim 61 wherein said memory is removable.

65. The method of claim 61 wherein said external interface is a card slot, and an interface card inserted therein, both compatible with a personal computer interface standard permitting removal and replacement of said interlace card without restarting operation of said processor.

66. The method of claim 65 wherein said interface card comprises an analog to digital converter.

67. The method of claim 61 further comprising operating said processor to perform a frequency transformation of said first and/or second data.

68. The method of claim 61 further comprising providing a sensor power supply for supplying power to said analog machine activity sensor.

69. The method of claim 68 wherein said sensor power supply is responsive to a control signal from said portable computer to activate or deactivate said analog machine activity sensor, and further comprising operating said portable computer to produce a control signal to activate said sensor power supply prior to collecting data from said analog machine activity sensor.

70. The method of claim 68 further comprising providing an interface cord connecting said sensor power supply and said analog machine activity sensor to said portable computer.

71. The method of claim 68 wherein said sensor power supply comprises a sensor power supply battery, and further comprising providing a battery charger connectable to said sensor power supply battery to charge said sensor power supply battery.

72. The method of claim 61 further comprising storing machine identifications and associated measurement parameters for a plurality of machines in said memory.

73. The method of claim 72 further comprising transmitting information between said memory and a host computer, including at least one of
    data collected from said analog machine activity sensor,
    an identification of a machine, and
    measurement parameters.

74. The method of claim 72 further comprising operating said processor to interact with a user to select a machine identification, and then process data collected from said analog machine activity sensor in accordance with measurement parameters associated with said selected machine identification.

75. The method of claim 61 wherein said portable computer further comprises a display.

76. The method of claim 75 further comprising operating said processor to display data collected from said analog machine activity sensor on said display.

77. The method of claim 75 further comprising operating said processor to perform a frequency transformation of data collected from said analog machine activity sensor and display said frequency transformation on said display.

78. The method of claim 61 wherein said portable computer is a pen-based palmtop computer.

* * * * *

UNITED STATES PATENT AND TRADEMARK OFFICE
CERTIFICATE OF CORRECTION

PATENT NO. : 6,801,877 B2 Page 1 of 1
APPLICATION NO. : 10/178034
DATED : October 5, 2004
INVENTOR(S) : Schiltz et al.

It is certified that error appears in the above-identified patent and that said Letters Patent is hereby corrected as shown below:

Column 6, line 56, delete "Manual No. EEW0002D", insert --Manual No. EEW0002B--.

Column 7, line 5, delete "from a accelerating", insert --from an accelerating--.

Column 9, lines 1 and 5, delete "to a digital", insert --to digital--.

Column 9, line 38, delete "in art that", insert --in the art that--.

Column 14, line 33, Claim 65, delete "said interlace card", insert --said interface card--.

Signed and Sealed this

Tenth Day of October, 2006

JON W. DUDAS
*Director of the United States Patent and Trademark Office*